(12) United States Patent
Gibson, II

(10) Patent No.: US 8,900,119 B2
(45) Date of Patent: Dec. 2, 2014

(54) MALE ENHANCEMENT DEVICE

(76) Inventor: Dennis A. Gibson, II, Cape Girardeau, MO (US)

( * ) Notice: Subject to any disclaimer, the term of this patent is extended or adjusted under 35 U.S.C. 154(b) by 259 days.

(21) Appl. No.: 13/457,098

(22) Filed: Apr. 26, 2012

(65) Prior Publication Data

US 2013/0204080 A1    Aug. 8, 2013

Related U.S. Application Data

(60) Provisional application No. 61/491,176, filed on May 28, 2011.

(51) Int. Cl.
*A61F 5/00* (2006.01)

(52) U.S. Cl.
USPC .......................................................... 600/38

(58) Field of Classification Search
USPC ................................ 600/38–41; 128/844, 842
See application file for complete search history.

(56) References Cited

U.S. PATENT DOCUMENTS

| | | | | |
|---|---|---|---|---|
| 2,899,957 | A | * | 8/1959 | Briggs ............................. 600/39 |
| 3,683,901 | A | | 8/1972 | Wegener |
| 3,759,254 | A | | 9/1973 | Clark |
| 4,671,262 | A | | 6/1987 | West |
| 4,690,135 | A | | 9/1987 | Gerow |
| 4,829,991 | A | | 5/1989 | Boeck |
| 6,036,635 | A | | 3/2000 | Altshuler |
| 6,098,626 | A | | 8/2000 | Kim |
| 6,298,852 | B1 | * | 10/2001 | Manning ....................... 128/844 |
| 6,537,204 | B1 | | 3/2003 | Elist |
| 6,796,311 | B1 | | 9/2004 | Zurakowski |
| 2004/0171911 | A1 | | 9/2004 | Zurita |
| 2005/0090708 | A1 | | 4/2005 | Low |
| 2006/0063971 | A1 | | 3/2006 | Hill |
| 2007/0093687 | A1 | | 4/2007 | Hoefer |
| 2007/0144529 | A1 | | 6/2007 | Bryant |
| 2010/0204542 | A1 | | 8/2010 | Hodge |

FOREIGN PATENT DOCUMENTS

RU    2034524 C1    5/1995

OTHER PUBLICATIONS

International Written Opinion of the International Searching Authority from co-pending PCT application No. PCT/US/2013/000115, filed Apr. 26, 2013.

* cited by examiner

*Primary Examiner* — Samuel Gilbert
(74) *Attorney, Agent, or Firm* — Grace J. Fishel

(57) ABSTRACT

A male enhancement device with a tubular body formed of a soft and pliable material such as silicone to increase the apparent length and girth of a wearer's penis for his partner's pleasure. The device has sidewalls of variable thickness around the circumference of the body to provide a thinned portion for placement by a user over his penile frenum and protuberances on an inner sidewall of the body. During sexual activity the tubular body lengthens and shortens as the protuberance slide along the wearer's penile shaft thus exaggerating the stroke for the wearer's pleasure.

13 Claims, 4 Drawing Sheets

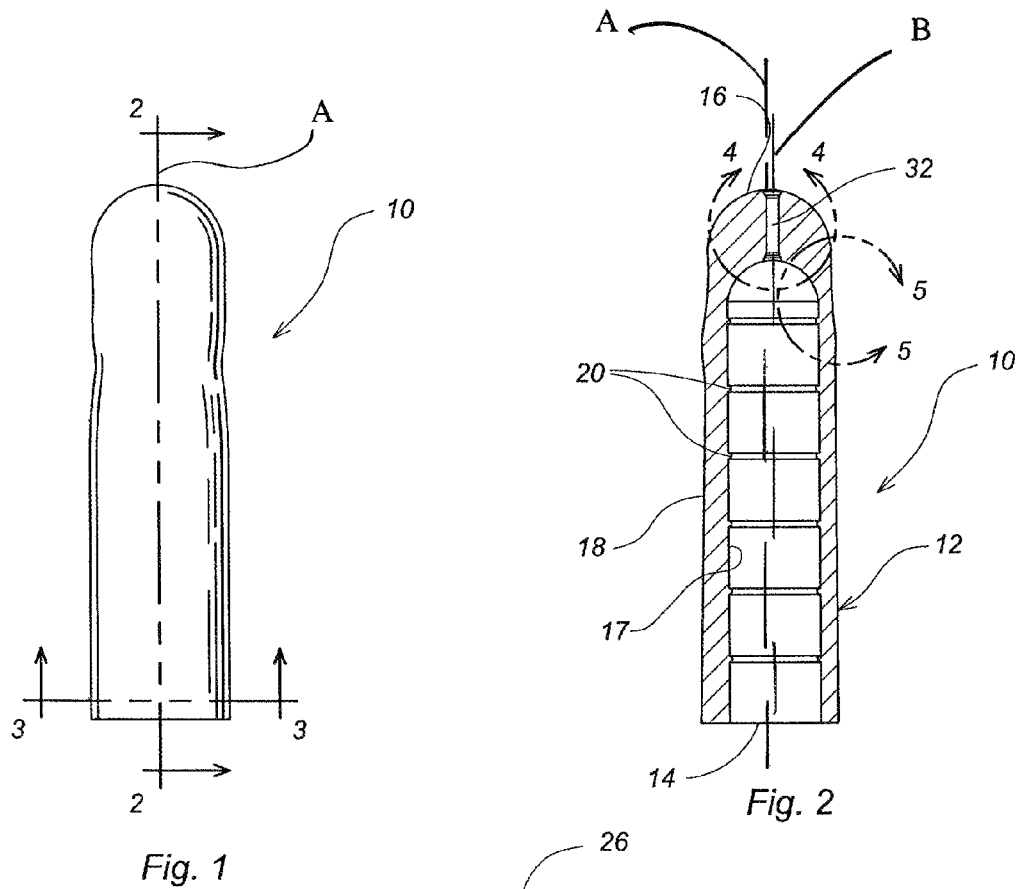
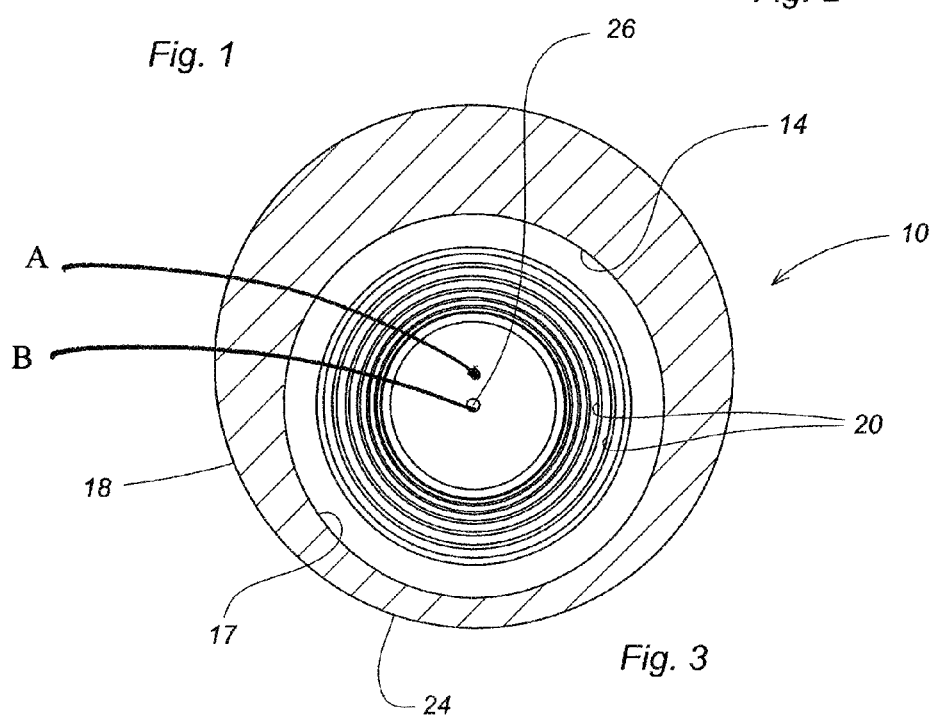

MALE ENHANCEMENT DEVICE

This application claims priority from provisional application Ser. No. 61/491,176, filed May 28, 2011, for Male Enhancement Device.

BACKGROUND OF THE INVENTION

1. Field of the Invention

The present invention relates to a male enhancement device for improving the sexual experience of a male user and his partner. The device may also be used independently by either sex.

2. Brief Description of the Prior Art

The augmentation in length and width of a penis for improved performance is of interest for the purpose of increasing the pleasure of a user's partner. Commercially available devices such as the Cyberskin Extension and the Vixen Ride On hard shell penile extension have disadvantages. The Cyberskin Extension is lifelike and slides on like a condom but it has thin walls which do not stabilize the extension's tip so that a user may find it necessary during intercourse to stop and straighten out the bent tip. The Vixen has a hard outer shell that numbs sexual sensation and is held in place with a rubber ring through which the testicles must first be passed and the penis then inserted into the hollow shell. There are also strapped or buckled on devices. None of which are satisfactory from the wearer's standpoint.

BRIEF SUMMARY OF THE INVENTION

In view of the above, it is an object of the present invention to provide a male enhancement device that produces an exaggerated stroke and motion transfer for the wearer's pleasure as well as increasing the apparent length and girth of the penis for his partner's pleasure. It is another object to provide a device which may be used by either sex independently. Other objects and features of the invention will be in part apparent and in part pointed out hereinafter.

In accordance with the invention, a male enhancement device includes a tubular shaped body closed at one end with an air passage in the closed end. The body has a sidewall of variable thickness about the circumference providing a thinned portion running along the body for placement by a user over his penile frenum. The inside of the body is preferably provided with a plurality of spaced apart protuberances. A seal is provided for the air passage to facilitate insertion of a user's penis into the device and then a vacuum seal during sexual intercourse. The device is formed of a life-like silicone material or another material having similar properties to facilitate heat transfer, exaggerated penile stroke and motion transfer.

The invention summarized above comprises the constructions hereinafter described.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which:

FIG. 1 is side elevation of a male enhancement device;

FIG. 2 is a cross-section taken along the plane of 2-2 in FIG. 1;

FIG. 3 is a cross-section taken along the plane of 3-3 in FIG. 1;

DETAILED DESCRIPTION OF THE INVENTION

Figure 4:
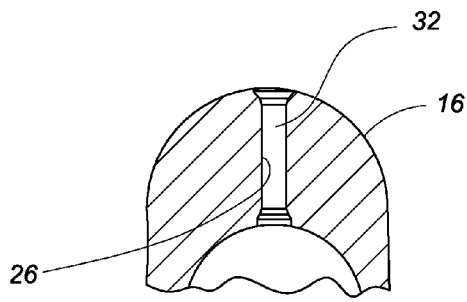
FIG. 4 is an enlarged view taken along the line of 4-4 in FIG. 2 showing a head of the male enhancement device closed with a plug for making an air seal.
Figure 5:
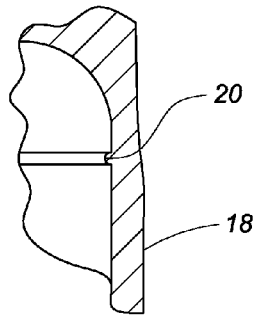
FIG. 5 is an enlarged view of a sidewall of the male enhancement device taken along the line of 5-5 in FIG. 2.
Figure 7:
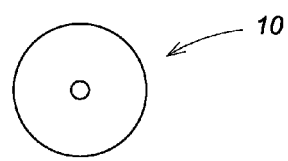
FIG. 7 is a plan view of the male enhancement device.

Referring to the drawings more particularly by reference character and beginning with FIGS. 1-5, reference character 10 refers to a male enhancement device in accordance with the present invention. Device 10 is formed of soft silicone rubber such as RTV silicone rubber sold by Silicones, Inc., Platinum-Cure Silicone Rubber sold by Reynolds Advanced Materials or anther stretchy, rubber-like material having similar properties.

Figure 8:
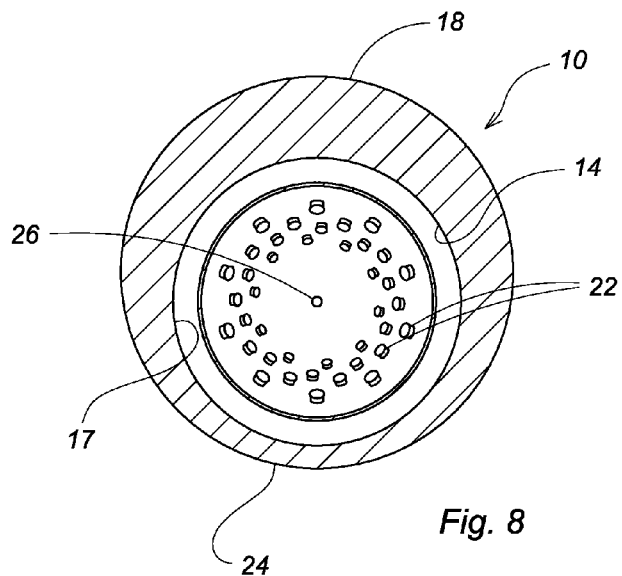
FIG. 8 is a cross-section similar to FIG. 3 showing a second male enhancement device.

Device 10 is a generally tubular shaped body 12 having an open proximal end 14 and a closed distal endwall 16. Body 12 has an inner sidewall 17 with a centerline axis A and an outer sidewall 18 with a centerline axis B, the axes of the inner and outer sidewalls are parallel but offset such that the wall thickness is variable around the circumference of the body as shown in FIG. 3. The inside of tubular body 12 is provided is a plurality of protuberances longitudinally laterally or diagonally spaced on inner sidewall 17 such as spaced apart annular ridges 20. Other structures such as knobs 22 as shown in FIG. 8 may be used but may provide too much stimulation. Knobs 22 may regularly arranged in a grid or another regular pattern or randomly arranged.

It has been found that for maximum pleasure, device 10 should be about 8 inches long and have an outside diameter of about 2½ inches. The spacing between inner and out sidewalls 17, 18 of body 12 may vary from about ½ inch to about ¼ inch providing a thinned portion 24 running the length of tubular body 12. An air passage 26 for use as described hereinafter is provided in closed distal endwall 16.

Figure 6:
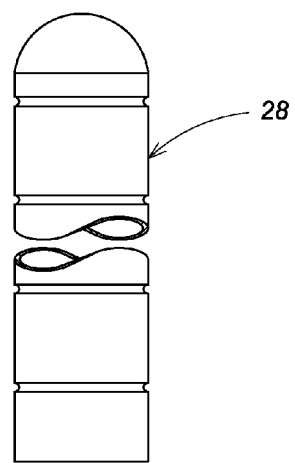
FIG. 6 is a side elevation of a sizing core for use with the male enhancement device.
Figures 12, 13:
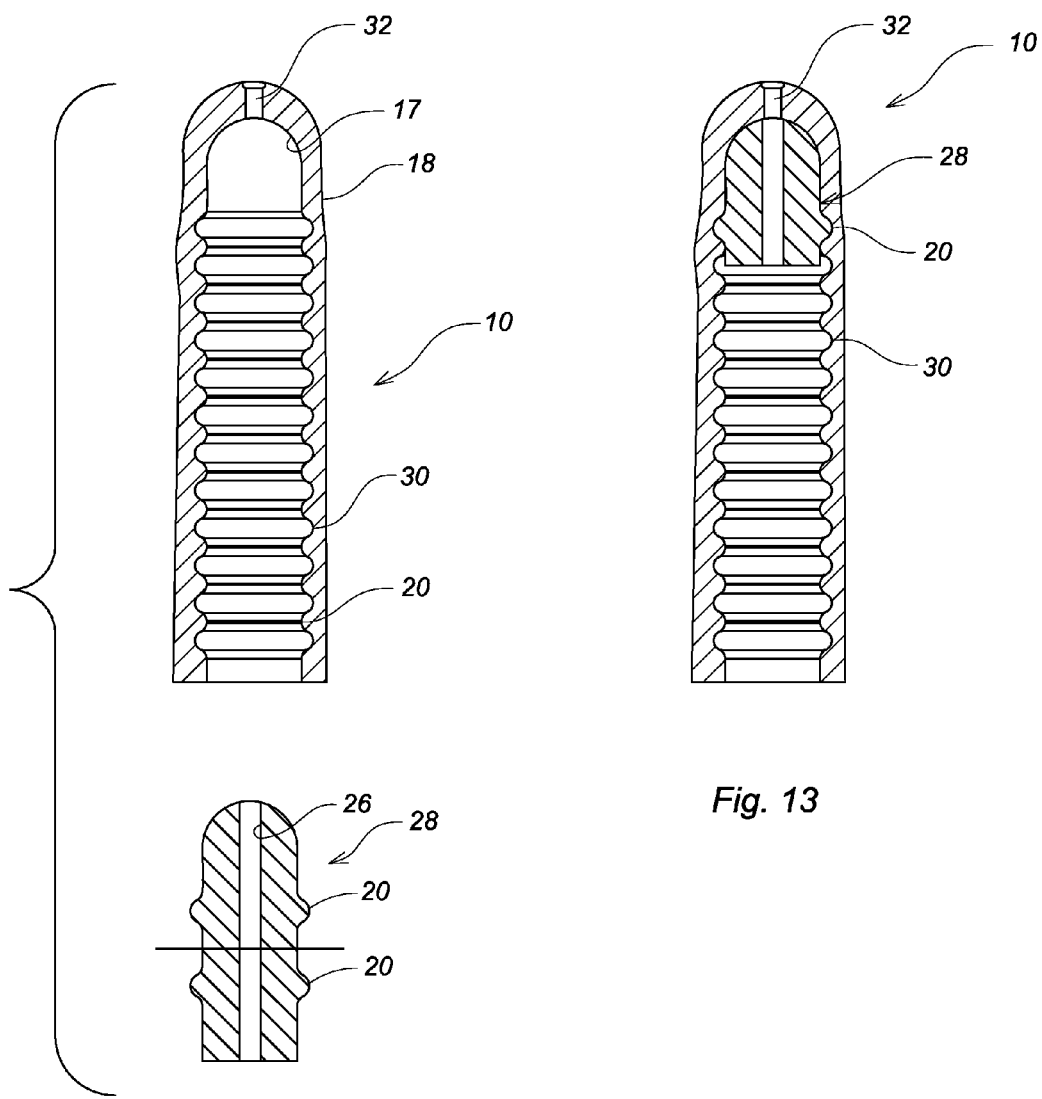
FIG. 12 is an exploded view of a third male enhancement device and a sizing core; and, FIG. 13 is an assembled view of the third male enhancement device and sizing core.

A solid cylindrical sizing core 28 as shown in FIG. 6 may be provided for inserting into device 10 and trimmed to length to adjust device 10 to the length of wearer's penis. Sizing core 28 includes a plurality of grooves 30 which are spaced apart such that when core 28 is inserted in device 10 they are in registry with ridges 20 for securing core 28 in device 10. As shown in FIGS. 12-13, ridges 20 on inner sidewall 18 are separated by complementary grooves 30 and complementary ridges 20 are provided on sizing core 28.

With air passage 26 open, device 10 may be slipped over an erect or semi-erect penis forcing excess air out of body 12. To facilitate insertion, the inside of body 12 may be provided with a lubricating film or substance and/or a biocide. Device 10 should be adjusted by the user such that thinned portion 24 of tubular body 12 is placed over the user's frenum, which is the sensitive part of a penis on the ventral side of the shaft between the glans and the base of the shaft.

Figure 9:
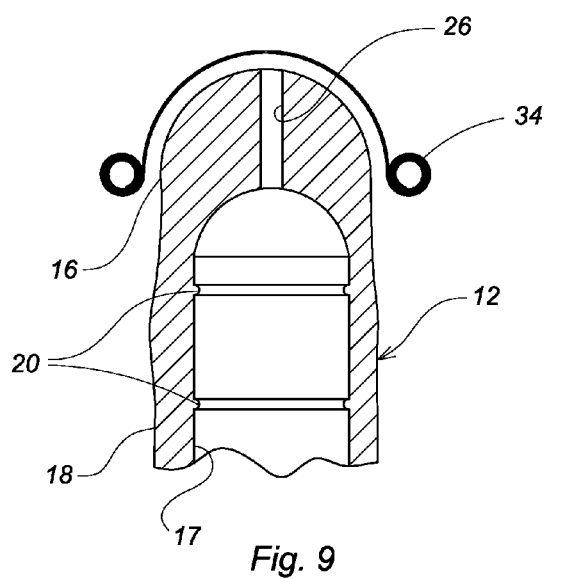
FIG. 9 is a cross-section similar to FIG. 4 showing a condom for use in making an air seal.
Figure 11:
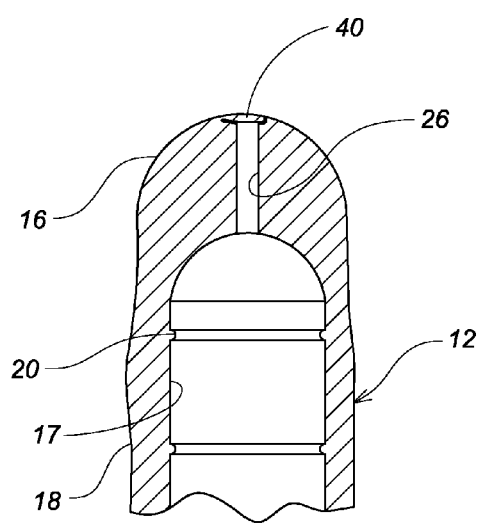
FIG. 11 is a cross-section similar to FIG. 4 of a male enhancement device wherein an air seal is formed with a flexible flap.
Figure 10:
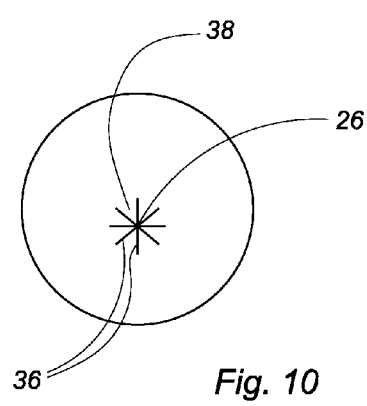
FIG. 10 is a plan view of a male enhancement device wherein an air seal is formed with flexible slits.

After the user has inserted his penis into device 10, air passage 26 is sealed with a plug 32 as shown in FIGS. 2 and 4 or with a condom 34 as shown in FIG. 9. Illustrative self-closing seals for this purpose include a plurality of radiating slits 36 with flexible tongues 38 as shown in FIG. 10, a flexible flap 40 as shown in FIG. 11 or the like. With this latter class of seals, the seal opens as a user inserts his penis into device 10 and air pressure builds up and then closes once pressure has been relieved. Whatever seal form used, the seal creates an ambient air pressure vacuum sufficient to prevent device 10 from slipping off during use.

During sexual activity with air passage 26 sealed, on an inward thrust of the penis, tubular body 12 is longitudinally compressed. On the outward pull, tubular body 12 lengthens and the protuberances slide along the user's penile shaft thus exaggerating the stroke. By motion transfer, his partner may also feel movement of protuberances against the sidewalls of the vagina particularly through thinned portion 24 of tubular body 12. Other pleasure benefits include the exchange of body heat which is transmitted through device 10 and, from the female standpoint, the length of device 10 ensures that the shaft of the user's penis stimulates the G-spot during intercourse. Width also plays an important role in vaginal orgasm.

From the above, it will be may be apparent that device 10 may also be used by either sex for self manipulation. For which purpose, females may slip device 10 over a vibrator or sizing core 28. It will also be understood that a vibrator may also be used during sexual intercourse.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed is:

1. A male enhancement device comprising a tubular shaped body with an open end and a closed endwall, said body having an inner sidewall with a centerline axis and an outer sidewall with a centerline axis, said axes of the inner and outer sidewalls parallel but offset such that a wall thickness between the inner and outer sidewalls is variable around the circumference of the body to provide a thinned portion for placement by a user over his penile frenum, said inner sidewall having laterally or diagonally spaced protuberances along a length of the inner sidewall, said closed endwall having an air passage with means to selectively block the passage of air whereby during sexual activity with air passage closed, on an inward thrust of a penis, tubular body shortens and on an outward pull the tubular body lengthens as the protuberances slide along the user's penile shaft.

2. The device of claim 1 wherein the endwall is thicker than the wall thickness between the inner and outer sidewalls.

3. The device of claim 1 wherein the protuberances are ridges spaced apart by complementary grooves.

4. The device of claim 1 wherein the protuberances are knobs.

5. The device of claim 4 wherein the knobs are regularly arranged.

6. The device of claim 1 molded of silicone rubber.

7. The device of claim 1 wherein the means to selectively block the passage of air is a plug.

8. The device of claim 1 wherein the means to selectively block the passage of air is a self closing seal.

9. The device of claim 1 wherein the means to selectively block the passage of air is a condom rolled over the closed endwall and down the outer sidewall of the body.

10. A male enhancement device molded of silicone rubber comprising a tubular shaped body with an open end and a closed endwall, said body having an inner sidewall with a centerline axis and an outer sidewall with a centerline axis, said axes of the inner and outer sidewalls parallel but offset such that a wall thickness between the inner and outer sidewalls is variable around the circumference of the body to provide a thinned portion for placement by a user over his penile frenum, said inner sidewall having ridges laterally spaced along a length of the inner sidewall and with complementary grooves along the inner sidewall, said closed endwall having an air passage with a plug to selectively block the passage of air, a solid cylindrical sizing core with ridges or grooves complementary to the grooves or ridges of the inner sidewall, said sizing core when inserted into the body to the closed endwall having an air passage in registry with the air passage in the closed endwall, whereby during sexual activity with the air passage in the body closed with the plug on an inward thrust of a penis, tubular body shortens and on an outward pull the tubular body lengthens as the ridges on the inner sidewall slide along the user's penile shaft.

11. The device of claim 10 wherein the sizing core may be cut to a selected length.

12. The device of claim 11 wherein the endwall is thicker than the wall thickness between the inner and outer sidewalls.

13. A male enhancement device molded of silicone rubber comprising a tubular shaped body with an open end and a closed endwall, said body having an inner sidewall and an outer sidewall, a solid cylindrical sizing core with one or more lateral grooves about an outer surface, said core configured to be inserted into the tubular body to the closed endwall and trimmable along the grooves to adjust the device to a length of a wearer's penis.

* * * * *